United States Patent
Chu

(10) Patent No.: US 8,317,675 B2
(45) Date of Patent: Nov. 27, 2012

(54) PELVIC IMPLANTS AND DELIVERY DEVICES AND METHODS OF USING THE SAME

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 942 days.

(21) Appl. No.: 12/244,071

(22) Filed: Oct. 2, 2008

(65) Prior Publication Data
US 2009/0093672 A1 Apr. 9, 2009

Related U.S. Application Data

(60) Provisional application No. 60/977,194, filed on Oct. 3, 2007.

(51) Int. Cl.
*A99Z 99/00* (2006.01)
(52) U.S. Cl. .......................... 600/30; 600/37
(58) Field of Classification Search .............. 600/30; 606/23.72, 119, 144, 151, 167, 190
See application file for complete search history.

(56) References Cited

U.S. PATENT DOCUMENTS

| | | | |
|---|---|---|---|
| 5,599,291 A | 2/1997 | Balbierz et al. | |
| 5,899,909 A | 5/1999 | Claren et al. | |
| 6,273,852 B1 | 8/2001 | Lehe et al. | |
| 6,491,703 B1 | 12/2002 | Ulmsten | |
| 6,592,610 B2 | 7/2003 | Beyar | |
| 6,612,977 B2 | 9/2003 | Staskin et al. | |
| 6,638,209 B2 | 10/2003 | Landgrebe | |
| 6,641,525 B2 | 11/2003 | Rocheleau et al. | |
| 6,691,711 B2 | 2/2004 | Raz et al. | |
| 7,112,171 B2 | 9/2006 | Rocheleau et al. | |
| 7,223,229 B2 | 5/2007 | Inman et al. | |
| 7,285,086 B2 | 10/2007 | Smith et al. | |
| 2003/0135225 A1* | 7/2003 | Harari et al. ............... | 606/151 |
| 2004/0225181 A1 | 11/2004 | Chu et al. | |
| 2005/0131391 A1* | 6/2005 | Chu et al. ................... | 606/1 |
| 2006/0089524 A1 | 4/2006 | Chu | |

FOREIGN PATENT DOCUMENTS

| | | |
|---|---|---|
| WO | 2003/034891 A2 | 5/2003 |
| WO | 2007/101970 A1 | 9/2007 |
| WO | WO 2007101970 A1 * | 9/2007 |

OTHER PUBLICATIONS

International Preliminary Report on Patentability for PCT Application No. PCT/US2008/078736, mailed on Apr. 15, 2010, 13 pages.

* cited by examiner

*Primary Examiner* — John Lacyk
*Assistant Examiner* — Joshua D Lannu

(57) ABSTRACT

An apparatus includes a first arm and a second arm coupled to the first arm. The second arm has a retracted configuration and an extended configuration. The first arm is configured to deposit a first end portion of an implant within a first portion of pelvic tissue when the second arm is in the retracted configuration. The second arm is configured to deposit a second end portion of the implant within a second portion of pelvic tissue on an opposite side of a urethra when in the extended configuration, such that a portion of the implant is positioned substantially beneath the urethra.

21 Claims, 18 Drawing Sheets

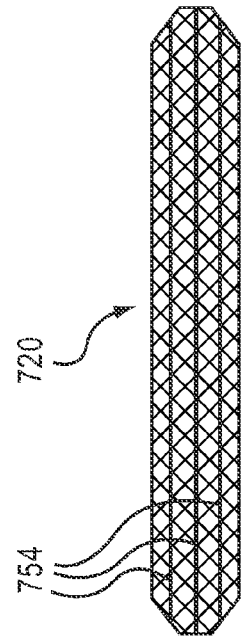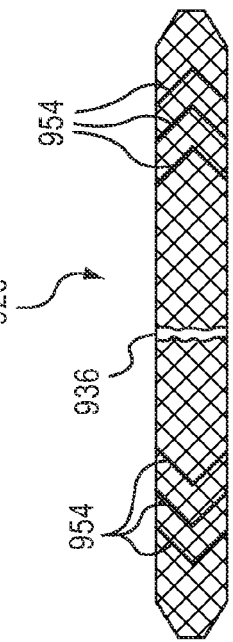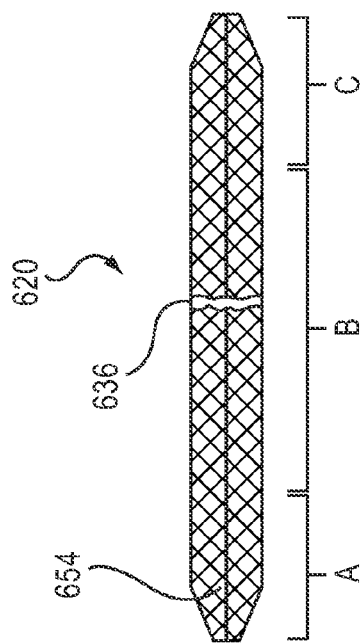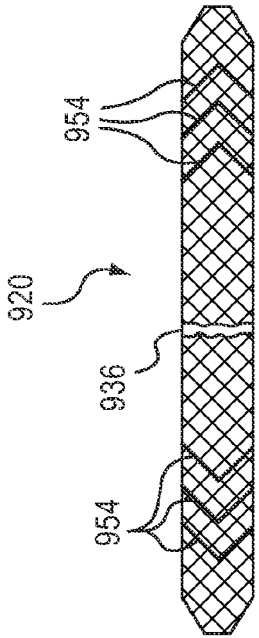

PELVIC IMPLANTS AND DELIVERY DEVICES AND METHODS OF USING THE SAME

CROSS-REFERENCE TO RELATED APPLICATIONS

This application claims priority to U.S. Provisional Application Ser. No. 60/977,194, entitled "Pelvic Implants and Delivery Devices and Methods of Using the Same," filed Oct. 3, 2007, the entire disclosure of which is hereby incorporated by reference in its entirety.

BACKGROUND

The disclosed invention relates generally to medical devices and more particularly to an implantable urethral sling and a device for implanting the urethral sling within a pelvic region.

A variety of medical procedures are performed to treat urinary incontinence in female patients, including the implantation of slings and other medical devices to support a urethra. Some procedures for the implantation of urethral supports include making multiple incisions in the patient, some being external to the patient's body. In such situations, the sling tension is often adjusted external to the patient's body. Some urethral supports are placed through a single vaginal incision and through an obturator membrane, but do not exit the external layer of skin of the patient. In such embodiments, sling adjustment and tensioning may be difficult and cumbersome due, for example, to the length of the sling. Often, the tension of the sling is adjusted manually during the sling placement in the limited space of the vaginal canal. In some cases, a sling can be adjusted by cutting the sling to a specific length before insertion within the pelvic region.

In some sling implant procedures, excess sling material is displaced deeper into the patient's body such as placing both ends of the sling deeper into the obturator. Unfortunately, such procedures can cause inadvertent injuries to nerves and blood vessels. In some applications where large dissections are performed, tissue in-growth can be inhibited or slowed causing further complications.

In some single incision implant procedures, the sling is pre-assembled to a delivery device for insertion into the pelvic region. Many single incision slings are minimal in length and such short association of the sling to a delivery device can limit the manipulation of the delivery device as a second end of the sling is being placed.

Thus, it would be desirable to have a urethral sling and a delivery device for implanting the urethral sling with minimal dissection and that can be inserted through a single small vaginal incision.

SUMMARY OF THE INVENTION

An apparatus includes a first arm and a second arm coupled to the first arm. The second arm has a retracted configuration and an extended configuration. The first arm is configured to deposit a first end portion of an implant within a first portion of pelvic tissue when the second arm is in the retracted configuration. The second arm is configured to deposit a second end portion of the implant within a second portion of pelvic tissue on an opposite side of a urethra when in the extended configuration, such that a portion of the implant is positioned substantially beneath the urethra.

BRIEF DESCRIPTION OF THE DRAWINGS

FIGS. 16-19 are top views of various additional embodiments of implants.

DETAILED DESCRIPTION

Figure 1:
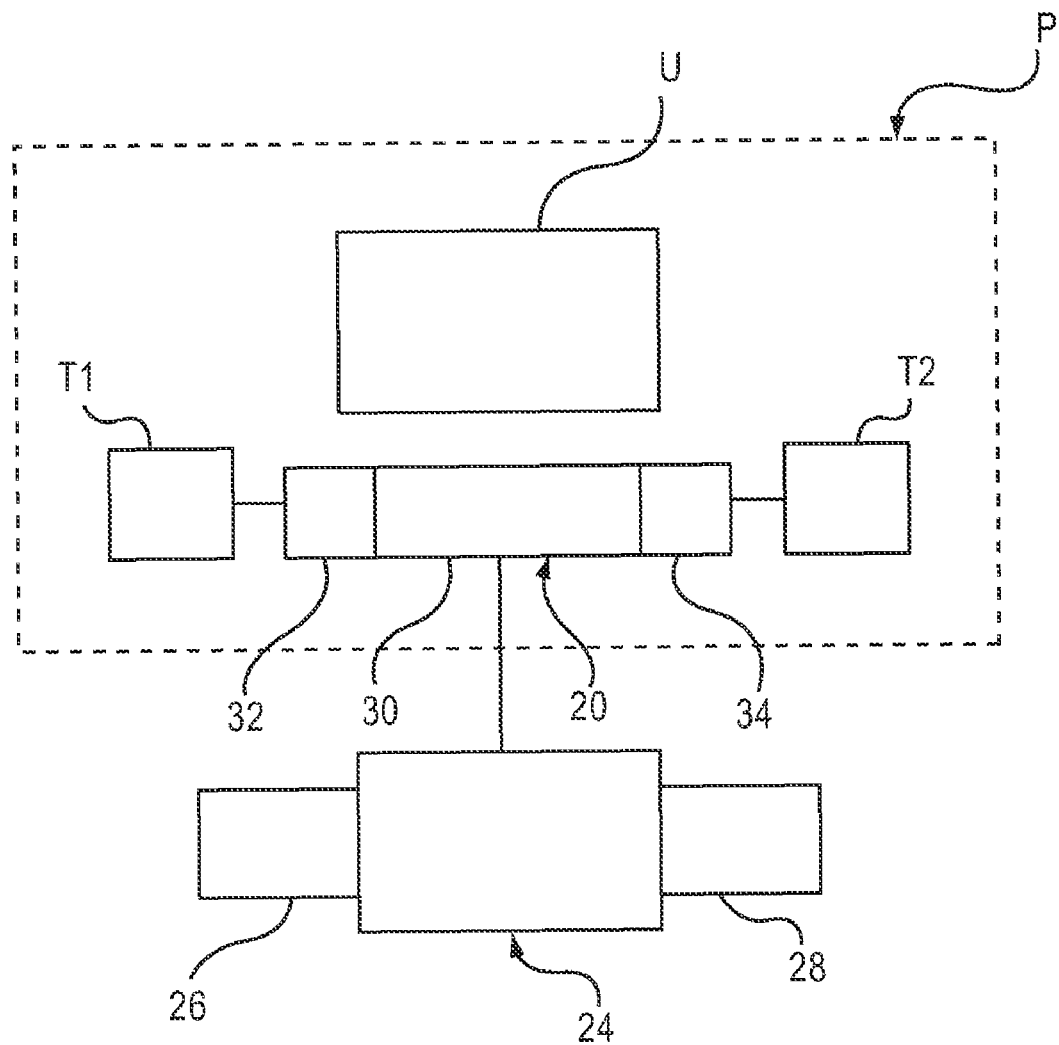
FIG. 1 is a schematic illustration of an embodiment of a delivery device and implant.

The systems and methods described herein are generally directed to the delivery and application of an implant (e.g., an urethral sling) to an anatomical site within a patient. For example, the systems and methods are suitable for sub-urethral implantation of an implantable sling into the periurethral tissue of a patient, with minimal dissection and a single small incision. In some embodiments, the sling can be placed and held within the periurethral tissue or fascia without piercing an obturator membrane or abdominal fascia. Devices and methods are described herein for treating urinary incontinence in a patient. The minimally invasive nature and efficacy of the devices enable procedures to be performed in a physician's office setting or in an operating room.

A sling or implant can include a tanged portion and a detanged portion. The tanged portion can be used, for example, to anchor or secure the implant to tissue. In some embodiments, the sling can include a strengthening member to reduce stretching of the implant and unraveling of the implant during implantation. For example, strands of the implant can be selectively melted and bonded along a longitudinal axis of the implant. In some embodiments, the implant is formed with a mesh material that is modified with a heat seal across its longitudinal axis. A sling can be implanted, for example, through a vaginal incision, and placed bilaterally in a direction toward an obturator muscle, or in a retro-pubic direction (behind the pubic bone), or in a pre-pubic direction (in front of the pubic bone). In other embodiments, an implant can be placed in the direction of other anatomical structures as desired. Although a single vaginal incision procedure for treating incontinence is described herein, other procedures can be performed using the devices described herein to place, for example, straps, implants, etc. into tissue (such as muscle, fascia, and/or ligaments) in other pelvic floor procedures.

With the devices described herein a bilateral dissection using a finger is not necessary and in fact undesirable, as a finger dissection can make a passageway that is too large for the tangs of a mesh implant to grip to the interior surrounding tissue of the passageway. The delivery devices and methods described herein are sized and configured to create a passageway to allow securement of the mesh to the surrounding tissue in the passageway to allow tissue in-growth.

It is noted that, as used in this written description and the appended claims, the singular forms "a," "an" and "the" include plural referents unless the context clearly dictates otherwise. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, an end of a delivery device inserted inside a patient's body would be the distal end of the delivery device, while the end of the delivery device extending outside a patient's body would be the proximal end of the delivery device.

In one embodiment, an apparatus that can be used to deliver an implant into a pelvic region includes a handle, a first arm coupled to the handle, and a second arm coupled to the handle and having a retracted configuration and an extended configuration. The first arm is configured to deposit a first end portion of an implant within a first portion of tissue in a pelvic region of a patient and the second arm is configured to deposit a second end portion of the implant to a second portion of tissue on an opposite side of a urethra when in an extended configuration, such that a portion of the implant is positioned substantially beneath the urethra.

In another embodiment, an apparatus includes a handle and a first arm couplable to the handle. A second arm is couplable to the handle and has a length that is less than a length of the first arm. The first arm is configured to releasably couple a first portion of an implant thereto. The second arm is configured to releasably couple a second portion of the implant thereto. The apparatus is configured to deliver the implant to a pelvic region of a patient and deposit the first end portion of the implant in a first tissue portion and the second end portion of the implant in a second tissue portion.

In one embodiment, a method includes inserting at least a portion of a delivery device having an implant releasably coupled thereto into a vaginal incision in a patient. The delivery device has a first arm and a second arm. The second arm is in a retracted position during the inserting. A first end portion of the implant is deposited into a first portion of pelvic tissue. The second arm is moved to an extended configuration, and a second end portion of the implant is deposited into a second portion of pelvic tissue such that a middle portion of the implant is positioned substantially below a urethra of the patient.

A kit according to an embodiment of the invention includes a delivery device including a first arm and a second arm and a mesh implant releasably couplable to the delivery device. The implant has a first end portion and a second end portion each configured to anchor the implant within pelvic tissue such that a middle portion of the implant is disposed beneath a urethra. The first arm defines a window through which a portion of the first end portion of the implant is disposable.

FIG. 1 is a schematic illustration of an embodiment of an implant and an associated delivery device. An implant 20 can be, for example, an implantable urethral sling. In some embodiments, the implant 20 can be implanted within a different location within a pelvic region of a patient. The implant 20 (also referred to herein as a sling) can be delivered through a single incision within a vagina of a patient. The implant 20 can be formed with a mesh material to allow tissue in-growth to the implant after implantation. For example, the implant can be formed with a mesh material as described in U.S. Patent Pub. 2005/0038452 A1 to Chu, the disclosure of which is hereby incorporated by reference in its entirety. In some embodiments, the entire implant 20 can be formed with a mesh material, whereas in other embodiments, only a portion of the implant 20 is formed with a mesh material. The implant 20 can be monolithically formed. Alternatively, the implant 20 can be formed with multiple different materials and/or can include multiple different components coupled together.

The implant 20 includes an elongate body having a first end portion 32, a second end portion 34, and a middle portion 30. The first and second end portions 32 and 34 can include tangs or a tanged portion to grip or attach to a portion of tissue T1, T2 within a pelvic region P. The middle portion 30 can also include tangs or be untanged. The terms "tanged" or "tangs" as used herein mean roughened or jagged edges or areas, such as can result from cutting a woven or knit mesh material. The tangs enhance anchoring of the implant 20 within tissue, such as pelvic tissue, without the use of additional anchoring mechanisms or sutures. In some embodiments, an implant includes tangs on an edge along an entire length of the implant. In other embodiments, the implant includes tangs covering substantially all of an exterior surface of the implant. In some embodiments tangs are only on the end portions 32, 34.

An implant 20 can be a variety of different shapes, sizes and configurations depending on the particular need and/or medical treatment. For example, the implant 20 can be substantially rectangular, square, oval, elliptical, etc. The implant 20 can be formed with various widths, lengths and thicknesses. The implant 20 can be uniformly formed (e.g., the same thickness and/or width) along the length of the implant 20, or the dimensions of the implant can vary along its length. For example, the ends of the implant 20 can be tapered. A length of the implant 20 can be, for example, between 5 cm (1.9 inches) and 12 cm (4.7 inches). In other embodiments, the implant has a length of greater than 12 cm (4.7 inches). In yet other embodiments, the implant has a length of less than 5 cm (1.9 inches).

In some embodiments, a mark (not shown in FIG. 1) is disposed at a lengthwise center of the implant 20 to aid in the alignment of the implant 20 beneath a urethra. The implant 20 can also include one or more strengthening members (not shown in FIG. 1). In some embodiments, the strengthening member is in the form of a heat seal on the implant 20. For example, strands of the implant can be selectively melted and bonded along a longitudinal axis of the implant to reduce stretching and/or unraveling of the implant 20 during implantation. The strengthening member can extend along an entire length of the implant or only along a portion of the implant 20. Multiple strengthening members (e.g., heat seals) can be arranged in various patterns on the implant 20.

The implant 20 can be inserted into a pelvic region using a delivery device 24 configured to hold the implant 20 during delivery, and selectively release the implant 20 within a pelvic region. For example, the delivery device 24 can deposit each of the ends of the implant 20 at selected tissue sites TI and T2 within the pelvic region P, such that a middle portion 30 of the implant 20 is positioned beneath a urethra U of the patient. For example, in some procedures, the ends of the implant 20 are deposited into periurethral tissue. In some embodiments, the implant 20 is delivered to the selected tissue site without penetrating an obturator membrane or abdominal fascia. For example, in some embodiments, the implant 20 is delivered using an obturator approach and secured to an internus muscle. In some embodiments, the implant 20 is delivered to the selected tissue site using, for example, an obturator approach, penetrates the obturator membrane, and is secured to an externus muscle. An implant 20 can be secured to contralateral sides of a pelvic region to form a hammock or U-shaped configuration as described in more detail below.

The delivery device 24 can be used to deliver the implant 20 by placing the implant 20 from a vaginal incision bilaterally in a variety of different directions including, for example, in an obturator direction, a retro-pubic (behind the pubic bone) direction, or a pre-pubic (in front of the pubic bone) direction.

As schematically illustrated in FIG. 1, the delivery device 24 can include a first arm 26 and a second arm 28, each configured to releasably couple a portion of an implant 20 to the delivery device 24. In some embodiments, the first arm 26 is shorter in length than the second arm 28. In some embodiments, the first arm 26 is slidably coupled to the second arm 28. In some embodiments, the first arm 126 and the second arm 128 each have a width less than a width of the implant such that the edges of the implant (with or without tangs) can anchor within the surrounding tissue prior to being released from the delivery device. The use of each of the different styles of delivery device 24 is described in more detail below with reference to specific embodiments. The delivery device can also include a handle (not shown) that a physician can use to assist in maneuvering the delivery device 24 during the delivery of a implant 20 into a pelvic region. In some embodiments, the first arm 26 and/or the second arm 28 can be removably coupled to the handle.

Having described above various general principles, several example embodiments are now described. These embodiments are only examples, and many other configurations of an implant 20 and delivery device 24 are contemplated, and will be apparent to the artisan in view of the general principles described above and in the exemplary embodiments.

Figure 2:
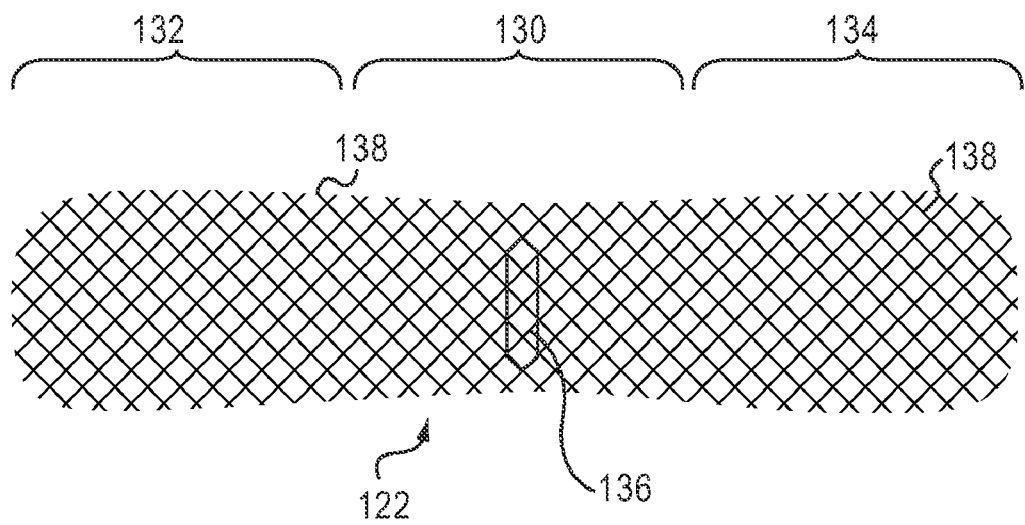
FIG. 2 is a top view of an embodiment of an implant.

FIG. 2 illustrates an embodiment of an implant. Implant 120 includes an elongate body 122 having a first end portion 132, a second end portion 134 and a middle portion 130. The implant 120 is formed with a mesh material and can include a center mark 136 that can be used to help align the implant underneath, for example, a urethra. The center mark 136 can be formed, for example, with a heat seal process by melting a strand or strands of the mesh material. Alternatively, the center mark 136 can be a mark placed on the implant with, for example, a marking instrument, providing a colorant that is biocompatible or otherwise suitable for use in medical devices.

As shown in FIG. 2, the first end portion 132 and the second end portion 134 each have tanged edges 138 (also referred to as tangs) formed therein, and the middle portion is untanged (or detanged, such as by heating or melting tangs formed when the mesh material is cut to form the edge of the implant). The tanged edges help retain the implant within bodily tissue such as pelvic tissue. The mesh material of the implant also allows for in-growth of the surrounding tissue. The first end portion 132 and the second end portion 134 can each have a tapered end, which helps with the deployment of the implant within a tissue by providing a narrower portion that can more easily pass through the pelvic tissue. In some embodiments, a length of the implant can be approximately 8 cm (3.1 inches). In some embodiments, the middle portion 130 can have, for example, a length of approximately 3.0 to 4.0 cm (1.2 to 1.5 inches) and the tanged end portions 132 and 134 can each have a length, for example, of approximately 2.0-2.5 cm (0.8 to 1.0 inch).

Figure 3:
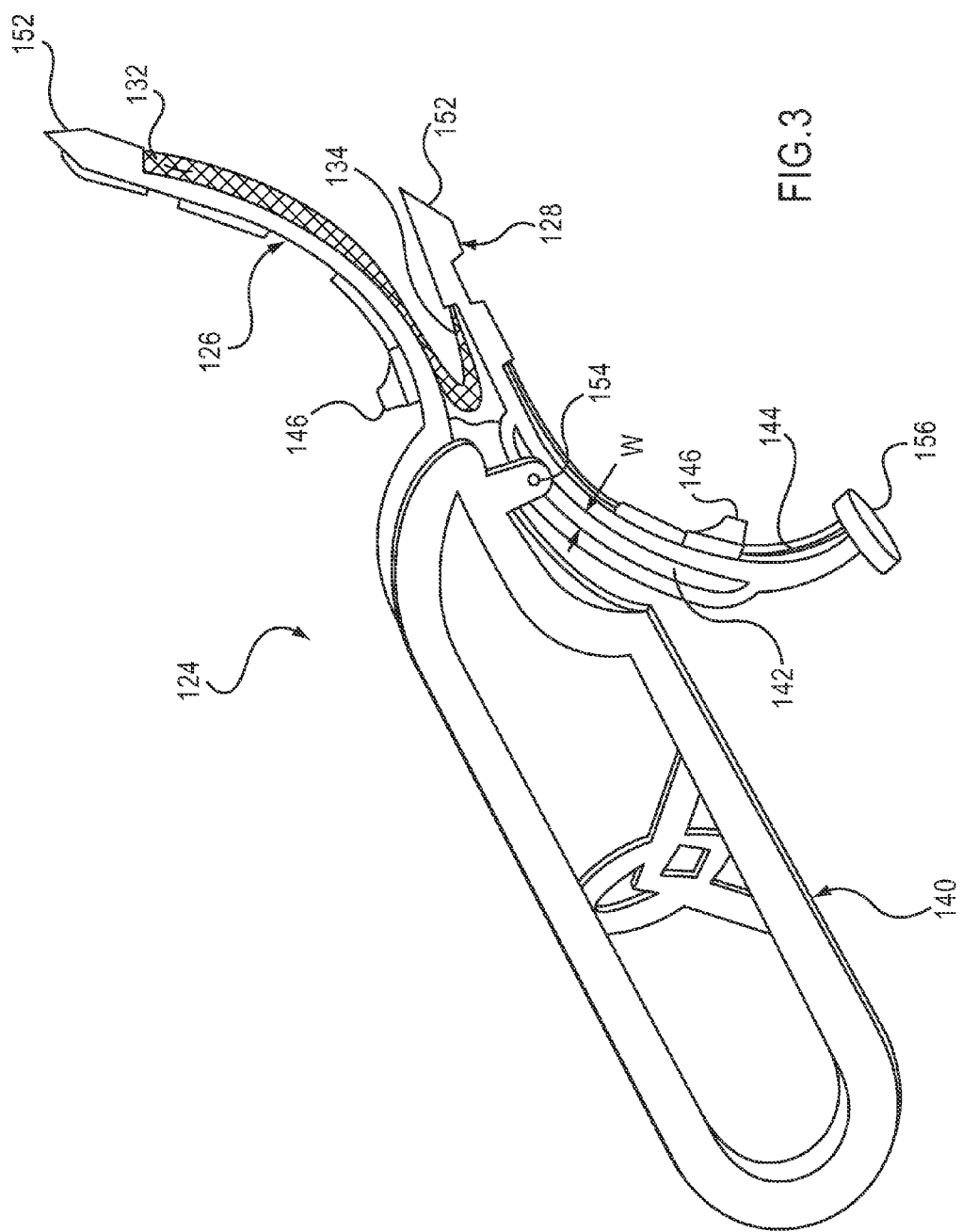
FIG. 3 is a side perspective view of another embodiment of a delivery device and implant shown in a retracted configuration.

An implant, such as the implant 120, can be delivered into a pelvic region of a patient using a delivery device 124, as shown in FIG. 3. The delivery device 124 includes a first arm 126, a second arm 128 and a handle 140. The second arm 128 is movably coupled to the handle 140 and the first arm 126. Specifically, in this embodiment, the second arm 128 defines a slot 142 that slidably couples the second arm 128 to the first arm 126, and to the handle 140, via a pin 154. A width W of the slot 142 can be sized such that it is substantially equal to an outer diameter of the pin 154 to frictionally hold the second arm 128 in a desired position relative to the pin 154. For example, the slot 142 can be sized such that the second arm 128 is frictionally held in the retracted position, as shown in FIG. 3, or whatever position the second arm 128 is placed in relative to the handle 140 and first arm 126.

The first arm 126 and the second arm 128 each have a tip 152 that preferably is sufficiently sharp to help penetrate tissue during delivery of the implant 120 into a pelvic region. A coupling member 144 is coupled to each of the first arm 126 and the second arm 128 and each coupling member 144 is coupled to a release button 146 disposed on the respective arm 126, 128. The coupling member 144 can be, for example, a wire. The coupling member 144 is used to releasably couple an implant, such as implant 120, to the delivery device 124 as will be described in more detail below. The release button 146 is used to activate and release the coupling member 144. For example, as shown in FIG. 4, the release button 146 can be moved in the direction of arrows A and B to move the coupling member 144 in the corresponding direction.

Figure 4:
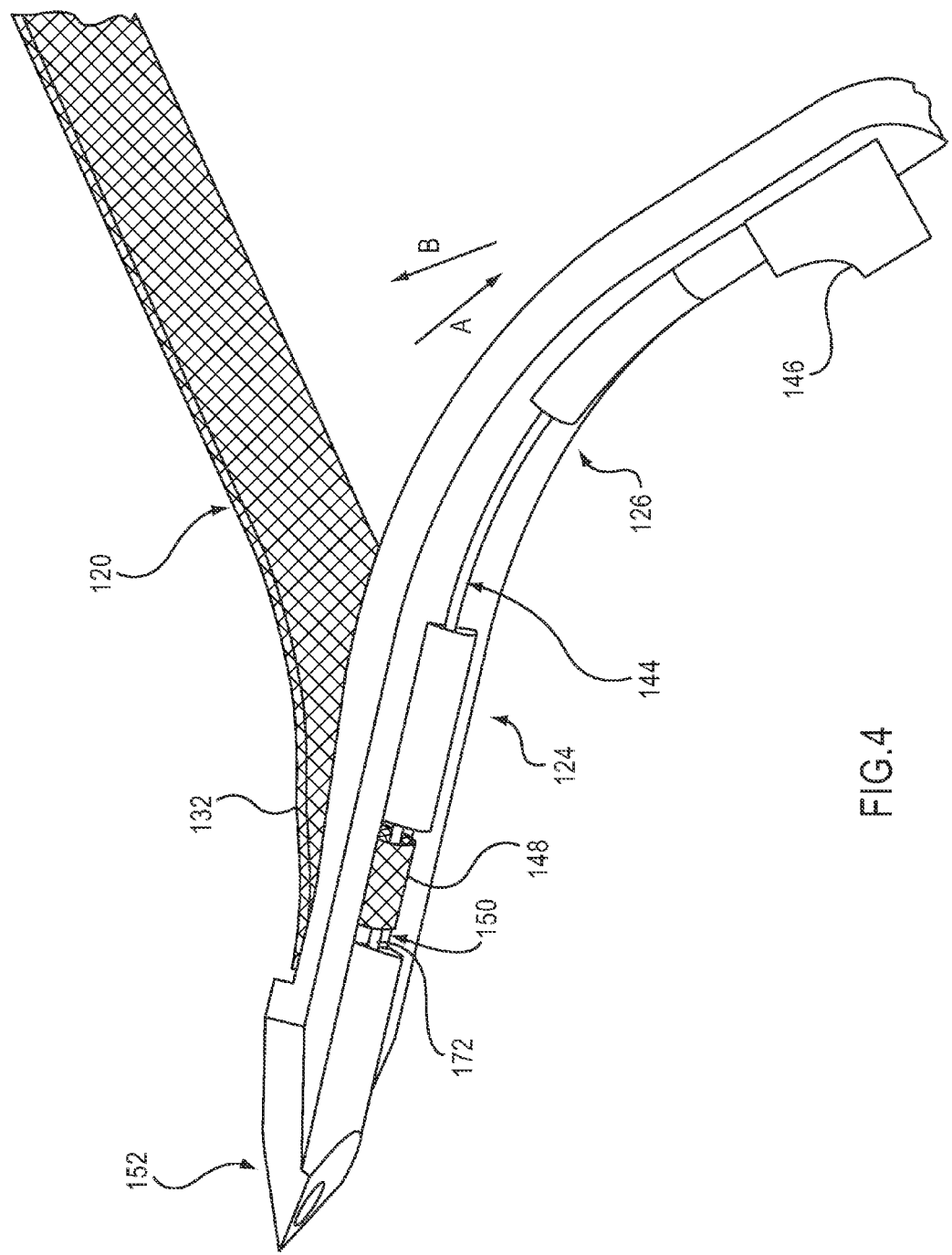
FIG. 4 is a side perspective view of a portion of the delivery device and implant of FIG. 3 shown in a skewered position.
Figure 5:
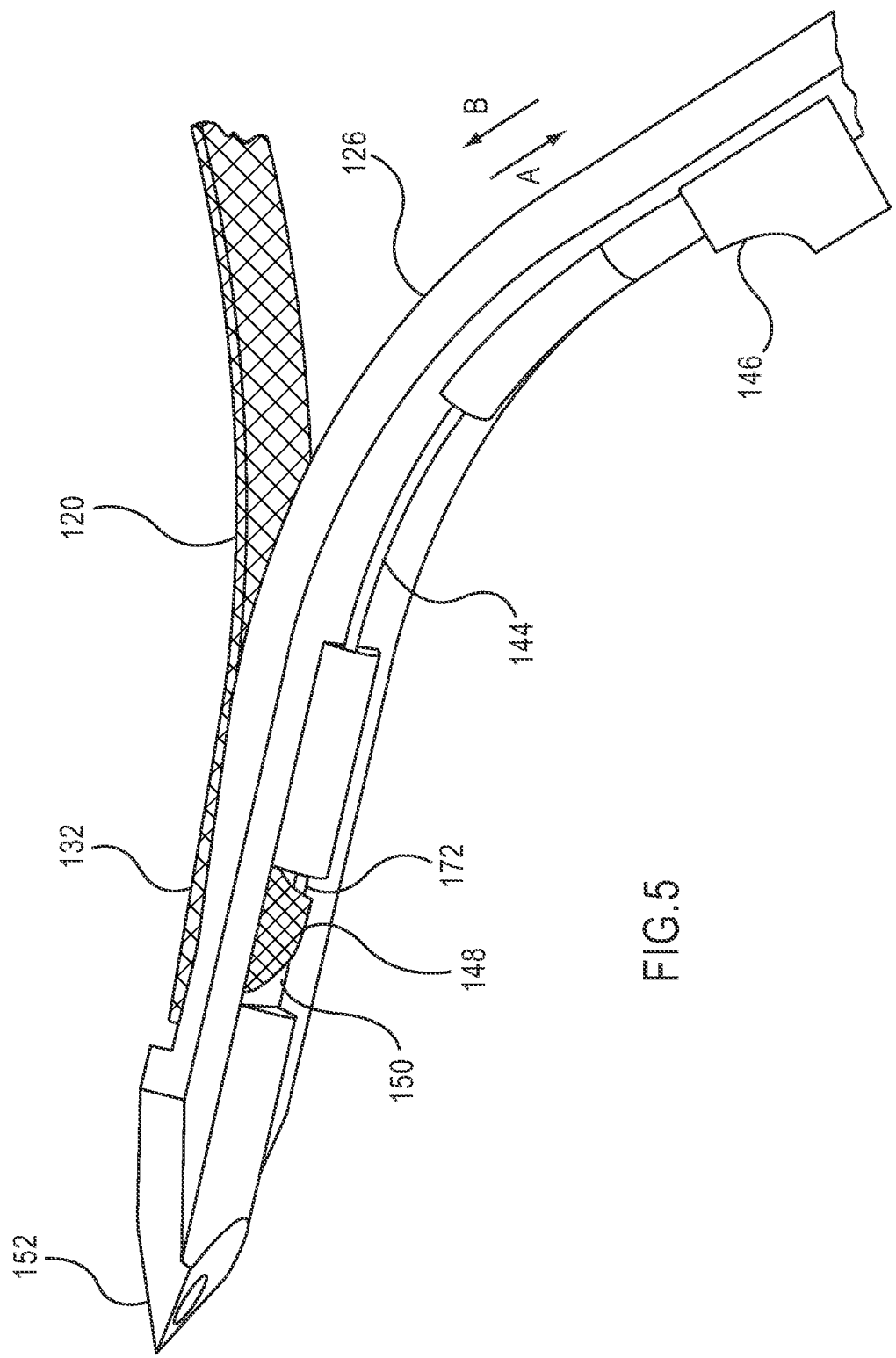
FIG. 5 is a side perspective view of a portion of the delivery device and implant of FIG. 3 shown in an unskewered position.

FIG. 4 illustrates a portion of the first end portion 132 of the implant 120 associated with or coupled to the first arm 126 of the delivery device 124. The first arm 126 is described in more detail with reference to FIGS. 4 and 5, however, it is to be understood that second arm 128 includes similar features and is configured in a similar manner as the first arm 126. The first arm 126 defines a window 150 through which a portion of the implant 120 can be disposed when the implant is coupled to the delivery device 124. To secure the implant 120 to the first arm 126 of the delivery device 124, the release button 146 is moved in the direction of arrow A, which causes a distal end 172 of the coupling member 144 to move to a proximal end of the window 150, as shown in FIG. 5. A portion 148 of the implant 120 is then placed or pushed into the window 150, as shown in FIG. 5. The release button 146 is then moved in the direction of arrow B such that the distal end 172 of the coupling member 144 is threaded through or skewers the portion 148 of the implant 120, as shown in FIG. 4, and is moved to a distal end of the window 150. To release the implant 120 from the first arm 126 of the delivery device 124, the release button 146 is moved in the direction of arrow A, which will move the distal end 172 of the coupling member back to the proximal end of the window 150 and unskewer the implant 120. Although a single coupling member 144 is shown on each arm of the delivery device, multiple coupling members can be used to secure the implant to the delivery device.

Prior to delivery of the implant 120 into a pelvic region, the first end portion 132 and the second end portion 134 are releasably coupled to the first arm 126 and the second arm 128, respectively, as described above using the coupling members 148. The implant 120 can be preloaded onto the delivery device 124 and presented to a physician as an assembly or kit, or the implant 120 and delivery device 124 can be provided separately and assembled by the physician. In some embodiments, the first arm 126 and the second arm 128 each have a width less than a width of the implant such that the tangs of the implant can anchor within the surrounding tissue prior to being released from the delivery device.

Figure 6:
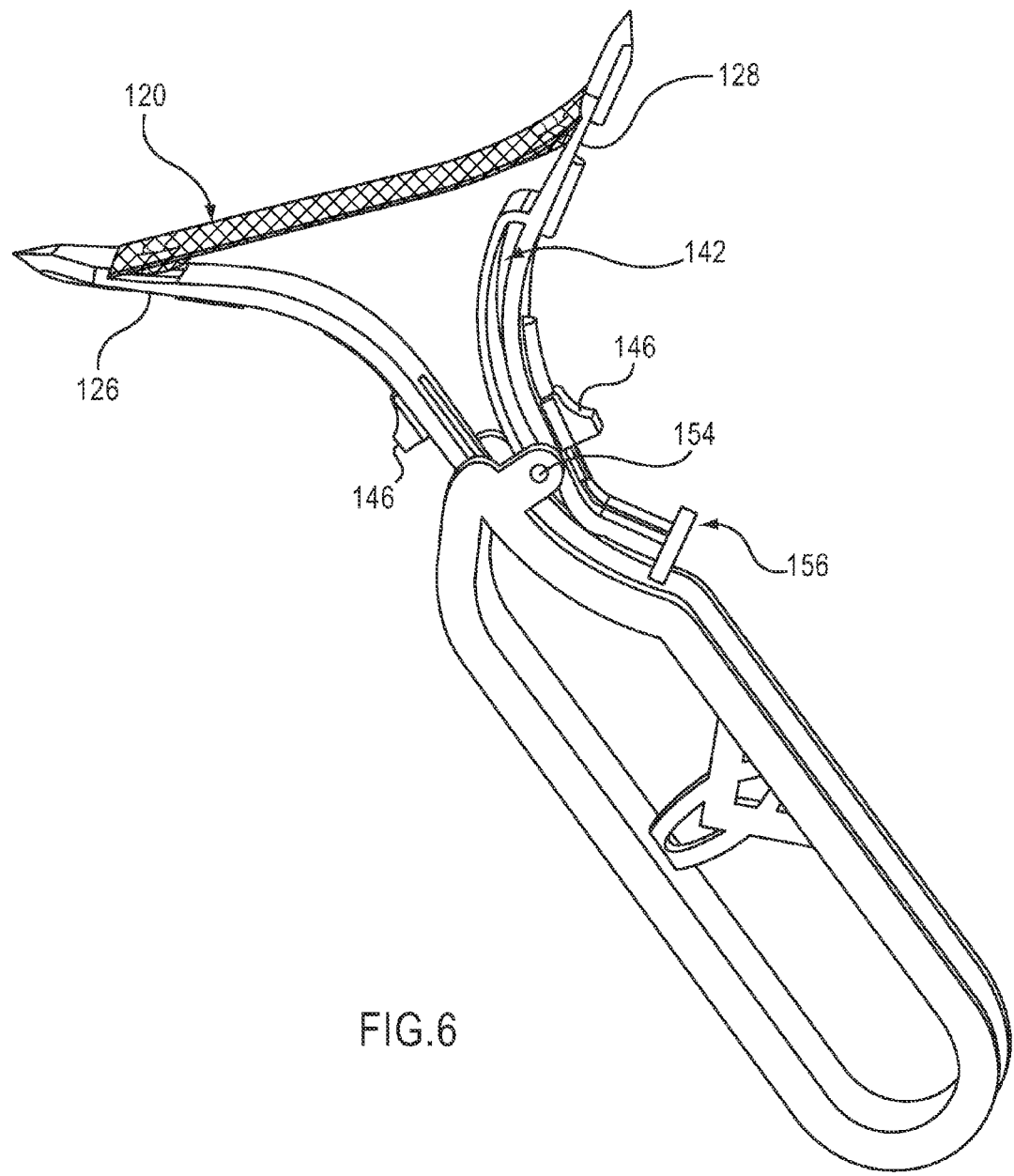
FIG. 6 is side perspective view of the delivery device and implant of FIG. 3 shown in an extended configuration.

FIG. 6 illustrates the delivery device 124 with the second arm 128 in an extended position used for deployment of the second end 134 of the implant 120. To move the second arm 128 from the retracted position (FIG. 3) to the extended position, an advancement button 156 is pushed, to move the second arm 128 along a path defined by the slot 142.

To prepare a patient for deployment of the implant 120 with a delivery device 124, the patient can be given local anesthesia injected along a medial aspect of the obturator foramina and anterior wall of the vagina. An incision is made along an anterior vaginal mucosa. The incision can be, for example, 1.5 to 2.0 cm (0.6 to 0.8 inches) in length and can extend approximately 0.5 cm (0.2 inches) to the meatus. The vaginal epithelium is dissected from the underlying periurethral fascia. The internal edge of an obturator foramen can be identified through palpation, for example at the level of the clitoris.

With the implant 120 loaded onto the delivery device 124, and the second arm 128 in the retracted position, the first arm 126 of the delivery device 124 can be inserted through the vaginal incision. The first arm 126 is gently pushed towards an internal edge of the obturator foramen and at the level of the clitoris. The advancement of the delivery device can be stopped, for example, when the center line of the implant 120 is approximately in-line with the clitoris. The second arm 128 is inserted through the vaginal incision. A small instrument, such as Metzenbaum scissors, can be placed between the implant 120 and the urethra to help ensure proper spacing is achieved between the urethra and the implant 120. The advancement button 156 is actuated to move the second arm 128 to the extended position. The second arm 128 is advanced towards an internal edge of an obturator foramen on an opposite side of the urethra and at the level of the clitoris. When the implant 120 is in contact against the small instrument, advancement of the second arm 128 is discontinued.

The implant 120 can be adjusted by further advancing or retracting the second arm 128, leaving approximately a 0.5 cm (0.2 inch) space between the urethra and the implant 120. The first end 132 and the second end 134 of the implant 120 are then deposited into the periurethral fascia by releasing the ends 132 and 134 of the implant 120 from the delivery device 124. The ends 132 and 134 can be released simultaneously or sequentially. As stated above, to release the implant 120 from the delivery device 124 the respective release buttons 146 are actuated to release or un-skewer the first end portion 132 and the second end portion 134 from the delivery device 124. The second arm 128 is then moved back to its retracted position, and the delivery device 124 removed from the patient. The tension of the implant 120 can then be checked and a multi-layer closure of the vaginal incision can then be performed.

Figure 7:
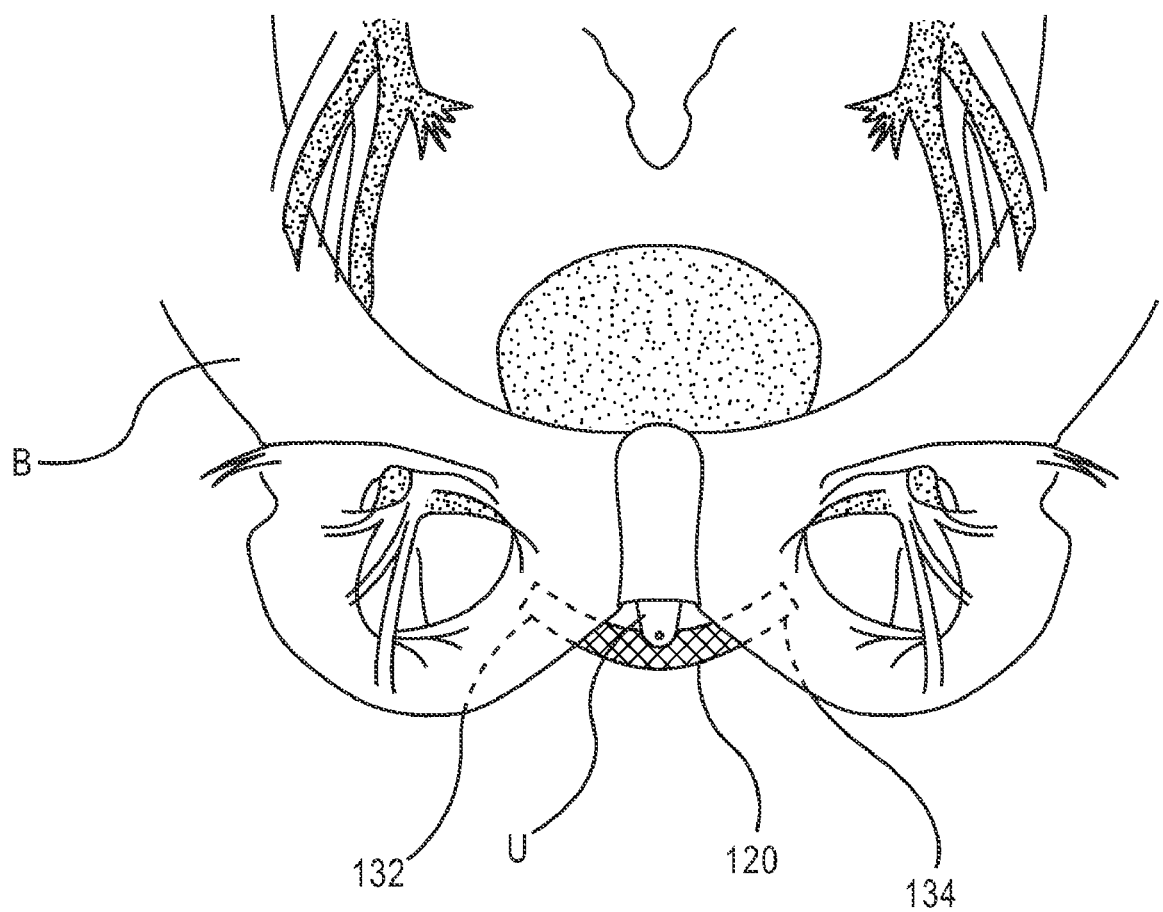
FIG. 7 is a front view of a portion of a pelvic region with the implant of FIG. 3 disposed therein.

FIG. 7 is a front view of a portion of a pelvic region illustrating the implant 120 placed within the pelvic region of a patient. As shown in FIG. 7, the implant 120 is placed behind the pubic bone B bilaterally from a vaginal incision towards the obturators. The first end portion 132 and the second end portion 134 are disposed on opposite sides of a urethra U such that the middle portion 130 is positioned substantially underneath the urethra U. This positioning of the implant 120 is sometimes referred to as a "hammock" configuration, as the implant forms a hammock under the urethra.

Figure 8:
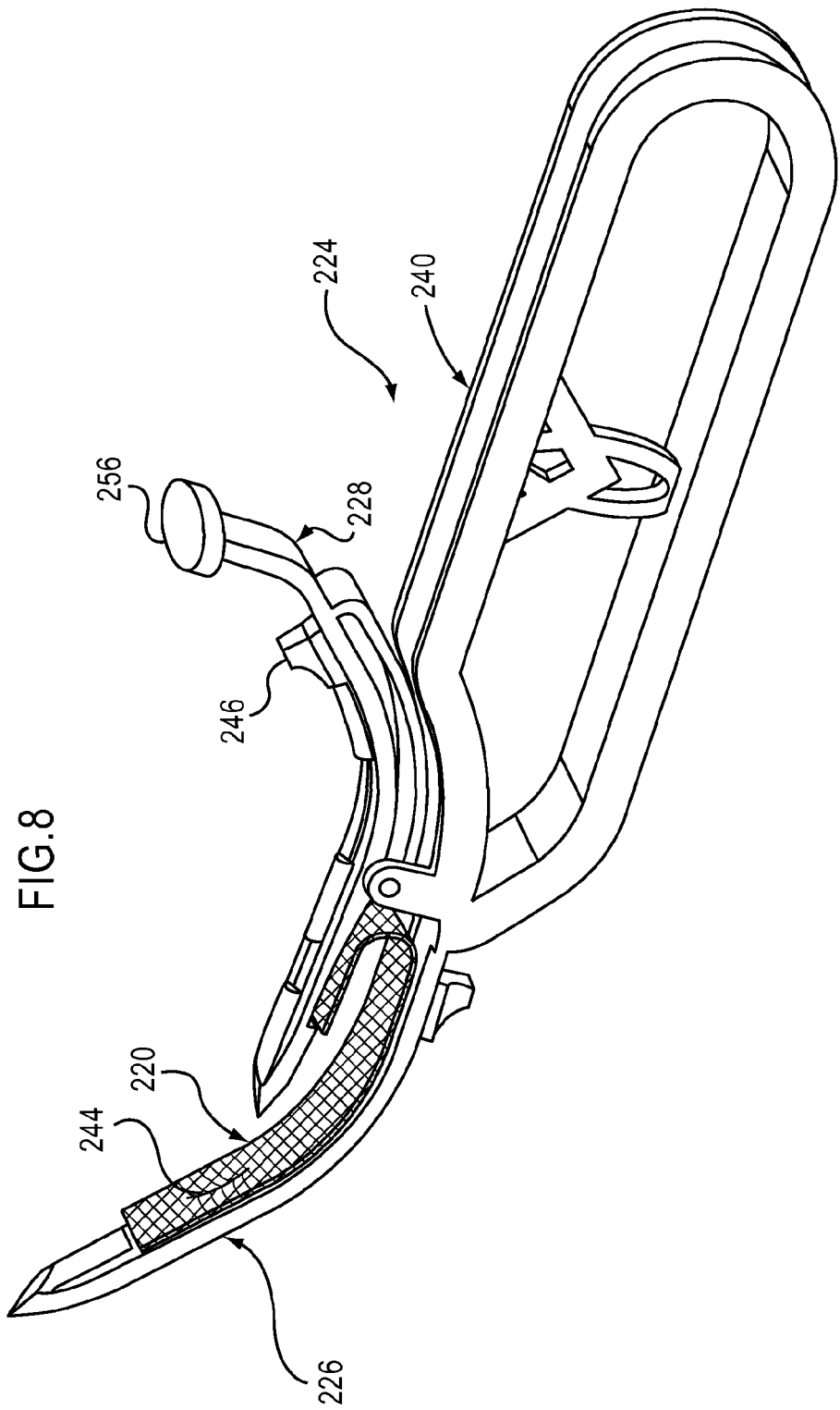
FIG. 8 is a side perspective view of another embodiment of a delivery device and implant.
Figure 9:
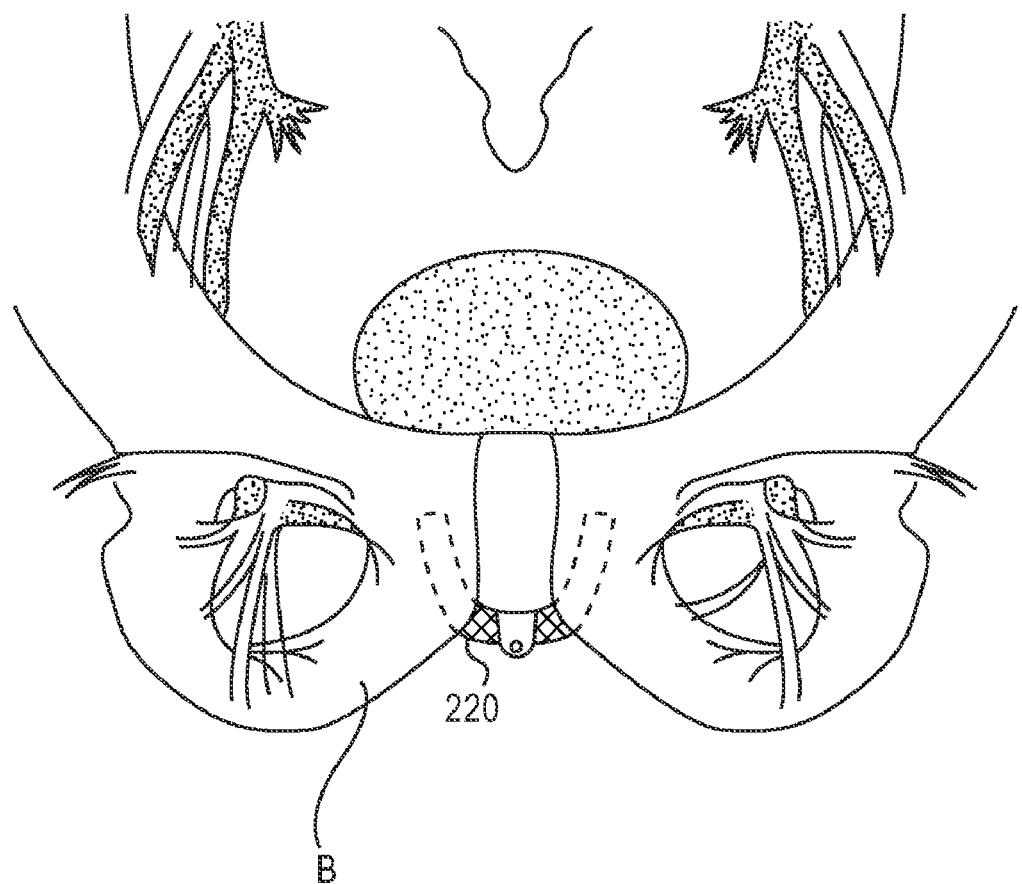
FIG. 9 is a front view of a portion of a pelvic region and the implant of FIG. 8 disposed in a retro-pubic position.
Figure 10:
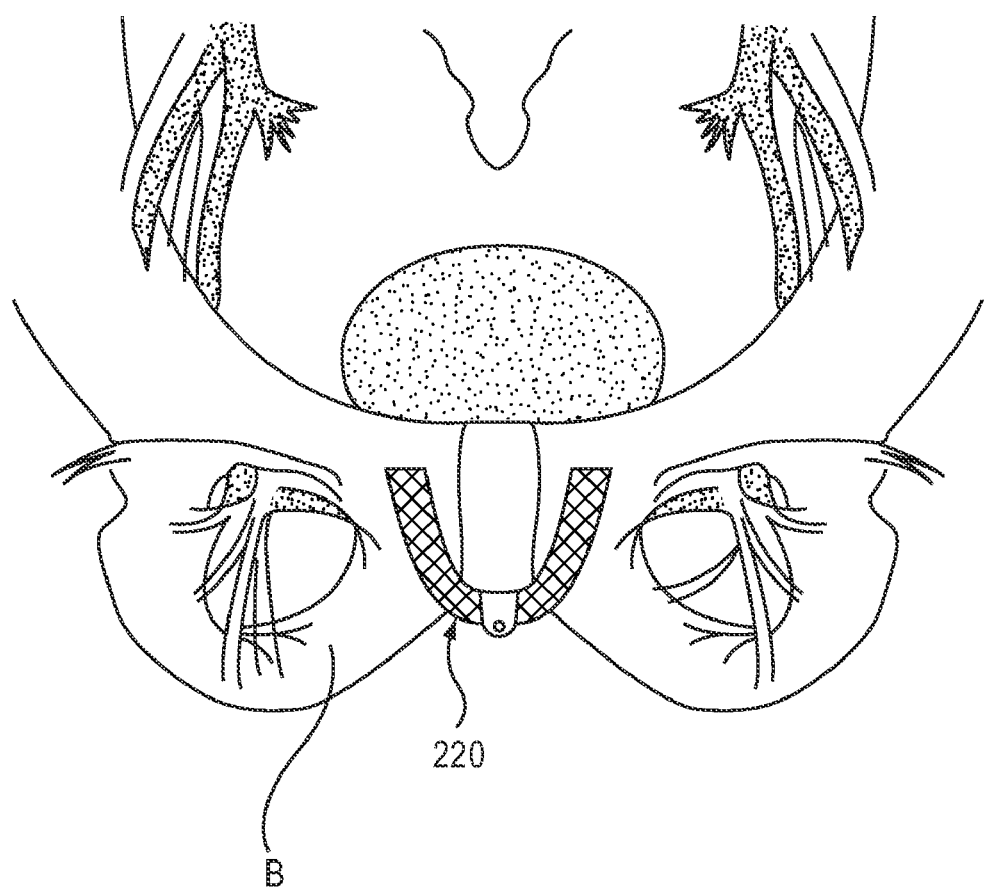
FIG. 10 is a front view of a portion of a pelvic region and the implant of FIG. 8 disposed in a pre-pubic position.

FIG. 8 illustrates an implant coupled to another embodiment of a delivery device. A delivery device 224 includes a first arm 226, a second arm 228 and a handle 240. The delivery device 224 is similar to delivery device 124, but the first arm 226 and the second arm 228 are angled such that the delivery device 224 can deliver an implant through a single vaginal incision and diverge the implant in a U-shaped configuration as shown in FIG. 9. In the U-shaped configuration of the implant 220 shown in FIG. 9, ends of the implant 220 are disposed in a laterally closer relationship to each other than in the previous embodiment shown in FIG. 7 (e.g., the hammock configuration). The implant 220 can be releasably coupled to the delivery device 224 in the same manner as described in the previous embodiment. For example, a release button 246 can be used to skewer and un-skewer the implant 220 via a coupling member 244, and an advancement button 256 can be used to move the second arm 228 between a retracted position and an extended position. With the implant 220 coupled to the first arm 226 and to the second arm 228, the delivery device 224 can be inserted through a single vaginal incision and deposited in pelvic tissue using a retro-pubic approach (behind the pubic bone B), as shown in FIG. 9, or using a pre-pubic approach (placed in front of the pubic bone B) as shown in FIG. 10.

Figure 11:
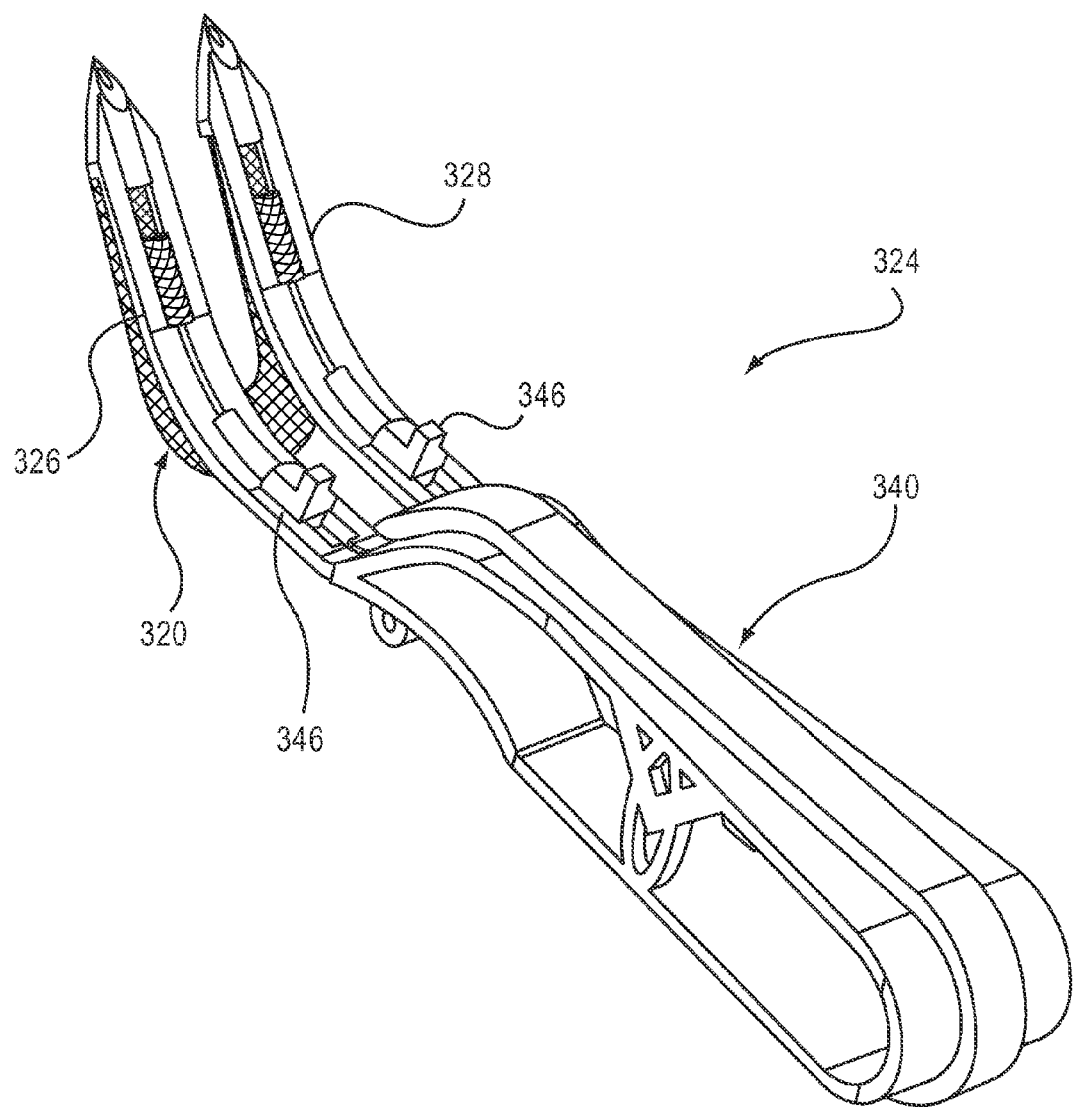
FIG. 11 is a side perspective view of another embodiment of a delivery device and implant.

FIG. 11 illustrates yet another embodiment of a delivery device that can be used to deliver a pelvic implant. A delivery device 324 includes a first arm 326, a second arm 328 and a handle 340. In this embodiment, the first arm 326 and the second arm 328 have substantially the same length and are malleable. The malleable arms allow a physician to bend the arms in a preferred position or direction before inserting the arms into the vaginal incision for placement. The malleability of the arms is such that after the physician has positioned the arms in the desired position, the arms will maintain that configuration. For example, the arms can be formed with annealed stainless steel, or for example, ⅛ to ¼ hard stainless steel. As shown in FIG. 11, an implant 320 can be releasably coupled to the arms 326 and 328 in the same manner as previously described for other embodiments. A release button 346 associated with each of the arms 326 and 328 and a coupling member (not shown) can be used to secure the implant 320 to and release the implant 320 from the arms 326 and 328. The first and second arms 326 and 328 can be released and delivered sequentially or simultaneously.

Figure 12:
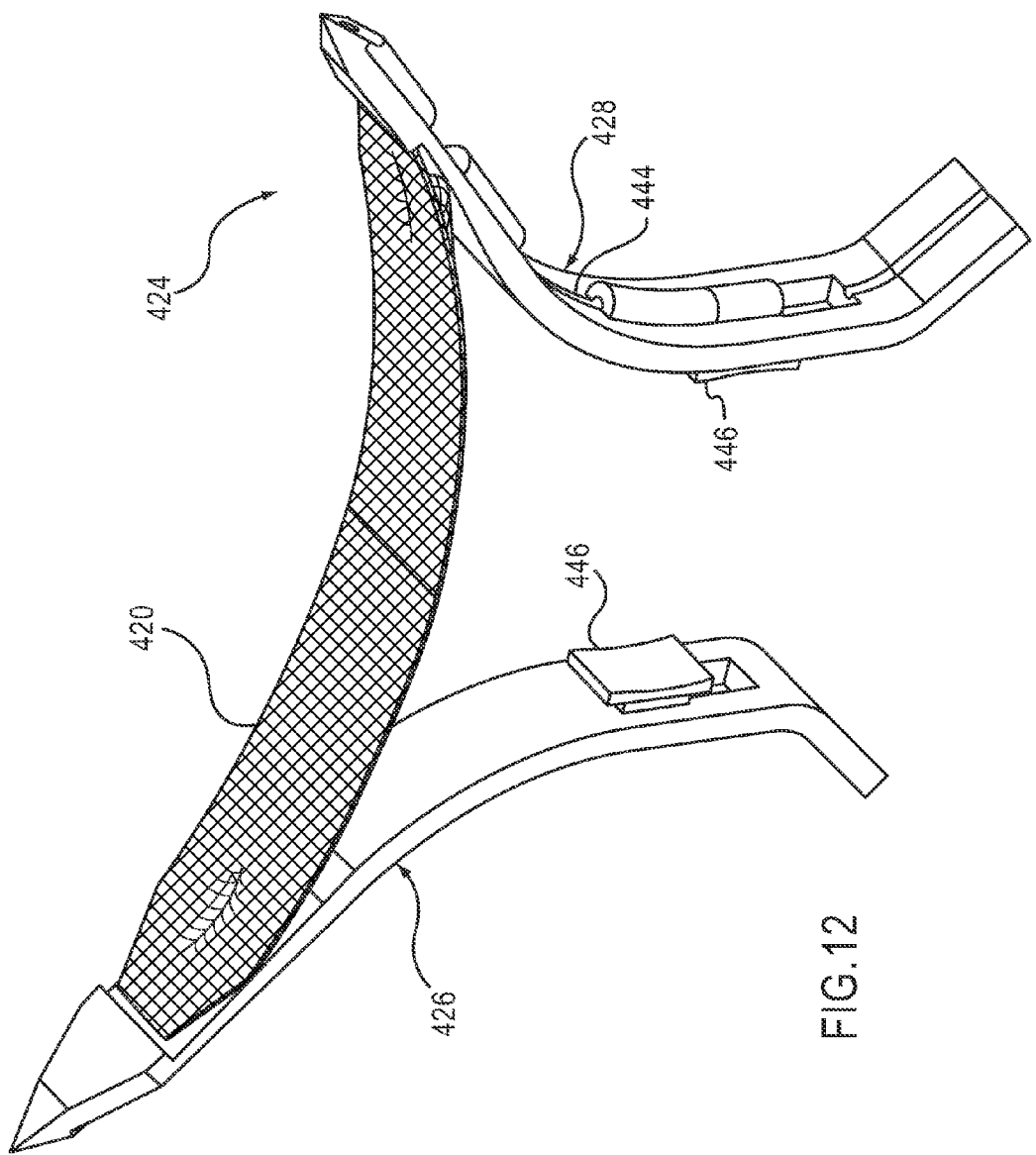
FIG. 12 is a side perspective view of a portion of another embodiment of a delivery device and an implant.

FIG. 12 illustrates a portion of an embodiment of a delivery device where the arms of the device are provided unattached to a handle. A delivery device 424 includes a first arm 426 and a second arm 428, each configured to releasably secure an end of an implant, such as an implant 420, thereto in a similar manner as described in previous embodiments. For example, the arms 426 and 428 each include a release button 446 that can be used to actuate a coupling member or skewer wire 444. The first arm 426 and the second arm 428 can be optionally coupled to a handle (not shown) prior to insertion into a vaginal incision. Alternatively, the first arm 426 and the second arm 428 can be inserted through a vaginal incision individually, without being coupled to a handle. In such a case, the arms 426 and 428 can optionally be coupled to a handle after being inserted. The arms 426 and 428 can be directed through the vaginal incision to deliver the implant 420 to a desired location within a pelvic region. The arms 426 and 428 can thus be supplied to a physician separately from the handle, which reduces the weight of the delivery device 424 during transport to the physician. It can also permit disposal of arms 426 and 428 after the procedure, but reuse of the handle with other arms in a subsequent procedure.

Figure 13:
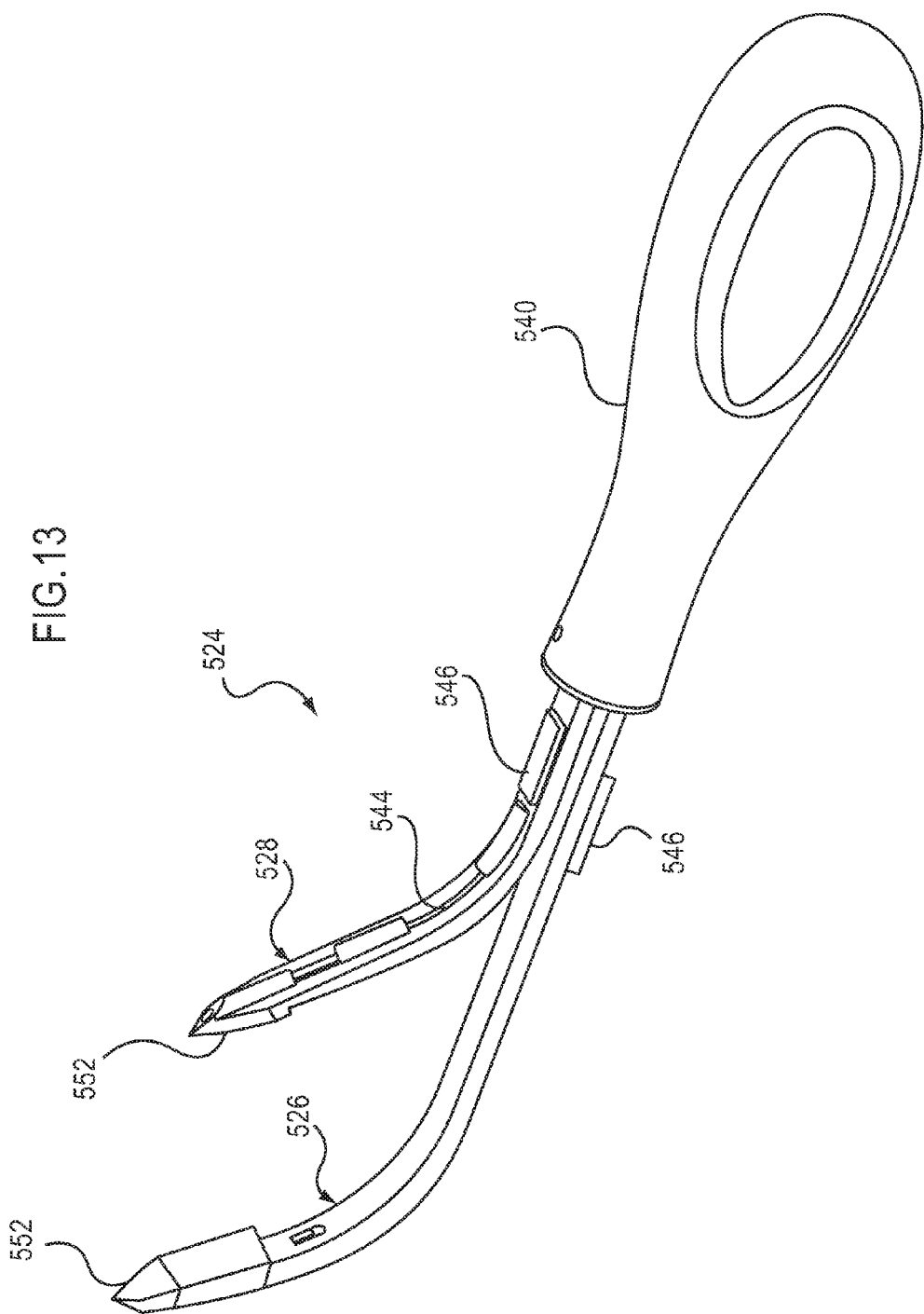
FIG. 13 is a side perspective view of another embodiment of a delivery device.

FIG. 13 is a side perspective view of another embodiment of a delivery device. A delivery device 524 includes a first arm 526, a second arm 528 and a handle 540. In this embodiment, the first arm 526 and the second arm 528 are removably couplable to the handle 540. In some embodiments, only one of the arms is removable. As shown in FIG. 13, the first arm 526 has a length greater than a length of the second arm 528. Each of the arms 526 and 528 can be formed with a malleable material similar to the embodiment of FIG. 11 to allow the arms 526 and 528 to be repositioned at various angles to meet the particular delivery approach desired. As with the previous embodiments, it may be desirable for the arms 526 and 528 to have a width that is less than a width of an implant to be loaded thereon such that tangs of the implant are allowed to engage the surrounding tissue. The arms 526 and 528 also have sharpened ends 552 to help penetrate tissue during implantation. In some embodiments, the arms have a blunt tip to dilate a tissue path.

Figure 14:
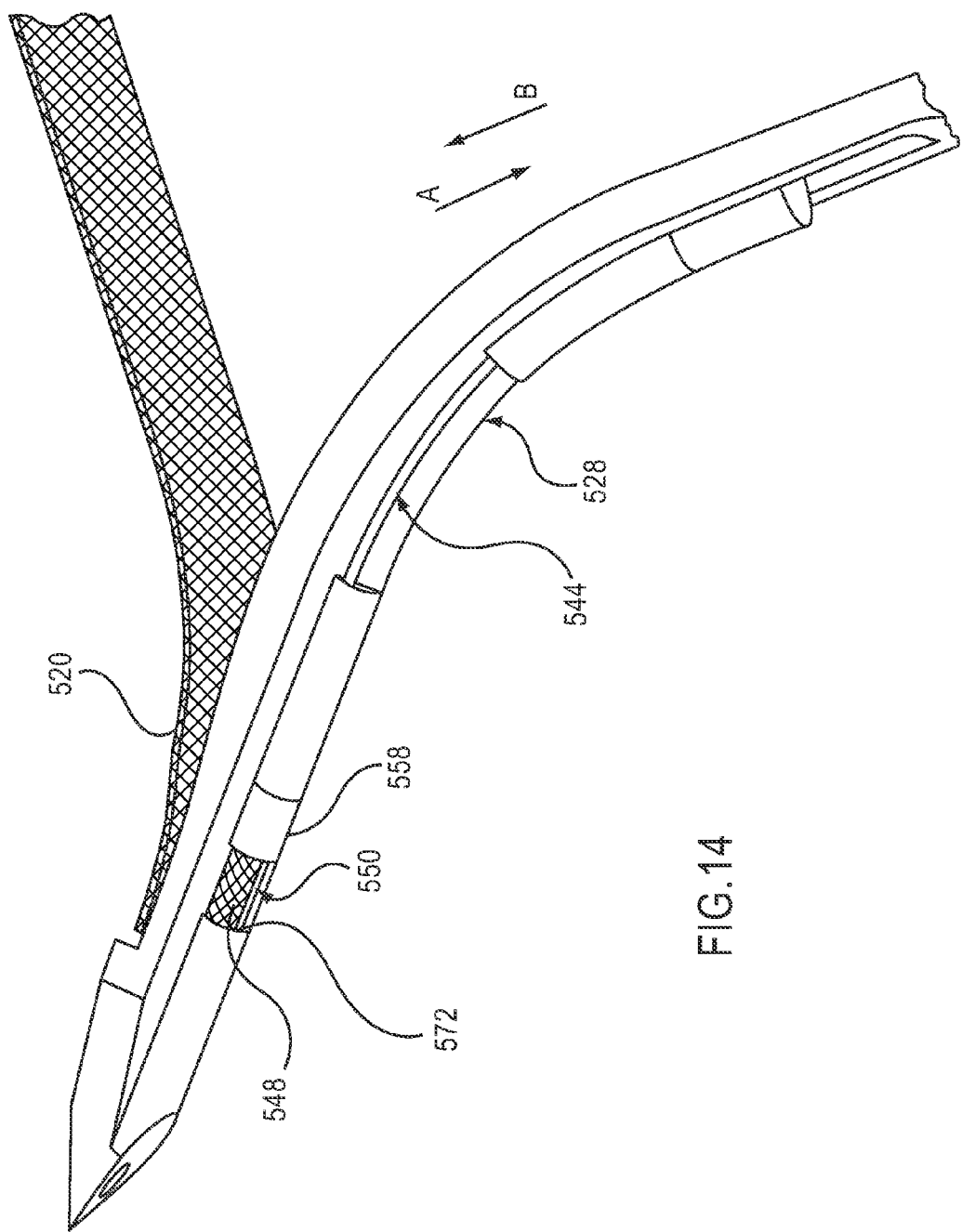
FIG. 14 is a side perspective view of another embodiment of a portion of the delivery device of FIG. 13 with a portion of an implant.

The delivery device 524 also includes a coupling member 544 (e.g., a wire) coupled to a release button 546 on each of the arms 526 and 528. In this embodiment, the coupling member 544 is coupled to a clamp 558 as best shown in FIG. 14. The clamp 558 is used to hold a portion 548 of the implant 520 within a window 550. As with the previous embodiments, the release button 546 can be actuated to move the coupling member 544, which will in turn move the clamp 558. Thus, a portion 548 of implant 520 can be pushed into the window 550 and the clamp 558 moved in the direction of arrow B to hold the portion 548 in place within the window 550 between the clamp 558 and an end wall 572 of the window 550. When the release button 546 is moved in the direction of arrow A, the clamp 558 will release the portion 548. As with previous embodiments, the delivery device 524 can be provided with an implant pre-loaded thereon, or the physician can load an implant at the time of delivery.

Figure 15:
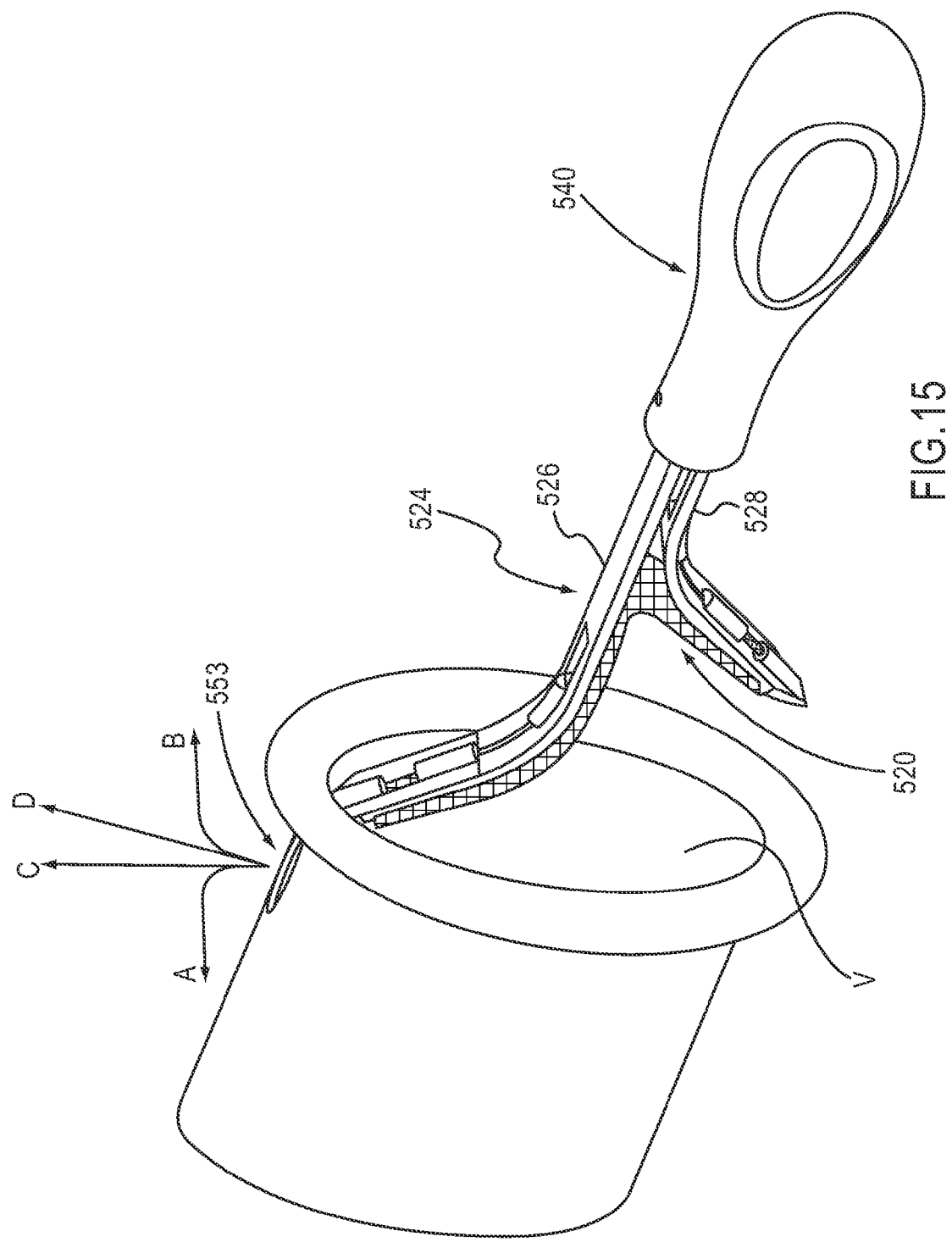
FIG. 15 is a side perspective view of the delivery device of FIG. 13 and an implant shown partially inserted within a schematic representation of a vagina.

To deliver the implant 520 into a pelvic region of a patient, the first arm 526 of the delivery device 524 is inserted into a vaginal canal V, as shown in FIG. 15. The first arm 526 can then be inserted through a vaginal incision 553 and maneuvered laterally in a direction toward, for example, an obturator or in a retro-pubic direction. For example, the arm 526 can be directed through the incision 553 and towards arrow A or B for the obturator approach or towards arrow C or D for the retro pubic approach. A pre-pubic approach can alternatively be used. The arm 528 can then be extended in a contralateral direction. The implant 520 can be deposited at a desired tissue site in the same manner as previously described by releasing the ends of the implant 520 from the delivery device.

FIGS. 16-19 illustrate alternative implant configurations. Each of the implants illustrated in FIGS. 16-19 includes at least one strengthening member and is formed from a mesh material. Each of the implants also includes tapered end portions. Although not explicitly illustrated in FIGS. 17-19, each of the implants can also have tanged and detanged portions as previously described.

As shown in FIG. 16, an implant 620 includes a center mark 636 and a single strengthening member 654 (e.g., a heat seal) that extends along a longitudinal length of the implant 620. The implant 620 also includes a first end portion and a second end portion, each having tanged edges as indicated at A and C, and a middle portion that is detanged as indicated at B.

FIG. 17 illustrates an implant 720 having three strengthening members 754 each extending along a longitudinal length of the implant 720. FIG. 18 illustrates an implant 820 having a center mark 836 and two strengthening members 854 that extend along only a portion of the implant 820. Lastly, FIG. 19 illustrates an implant 920 having a center mark 936 and multiple strengthening members 954 arranged in a pattern on each end portion of the implant 920.

Figure 20:
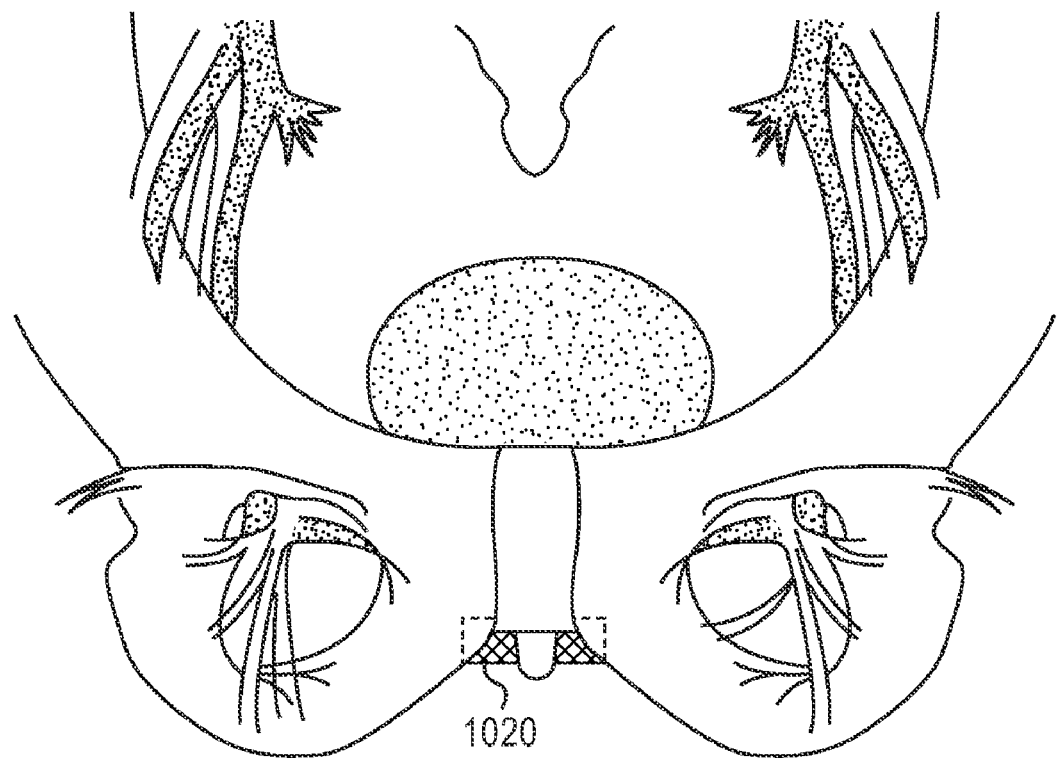
FIG. 20 is a front view of a portion of a pelvic region and another embodiment of an implant disposed therein.

FIG. 20 illustrates another embodiment of an implant shown disposed within a pelvic region. In this embodiment, an implant 1020 is shorter in length than the previous embodiments. For example, the implant 1020 can have a length of approximately 3 to 5 cm (1.2 to 1.9 inches). The implant 1020 can be placed through a vaginal incision using a delivery device as described herein. For example, the implant 1020 can be placed through an incision in an anterior vaginal mucosa, approximately 0.5 cm (0.2 inches) in length and distal to the meatus of the vagina. The vaginal epithelium is dissected bilaterally approximately 1.5 cm (0.6 inches) from the underlying periurethral fascia. The implant 1020 is then placed in the space created by the dissection.

The implant (e.g., implant, 20, 120, 220, etc.) can be formed with a variety of different materials, such as biocompatible plastics and/or metals. In some embodiments, the implant is formed with a mesh material to promote tissue in-growth. For example, the mesh used in the Advantage® sling system manufactured by Boston Scientific Corporation can be used. Alternatively, the implant can be formed with Polyform® material manufactured by Boston Scientific Corporation. The various components of the delivery devices described herein can also be formed with a variety of different biocompatible plastics and/or metals. For example, the arms of the delivery device can be formed from a polymer or stamped from, for example, a stainless steel.

Figure 21:
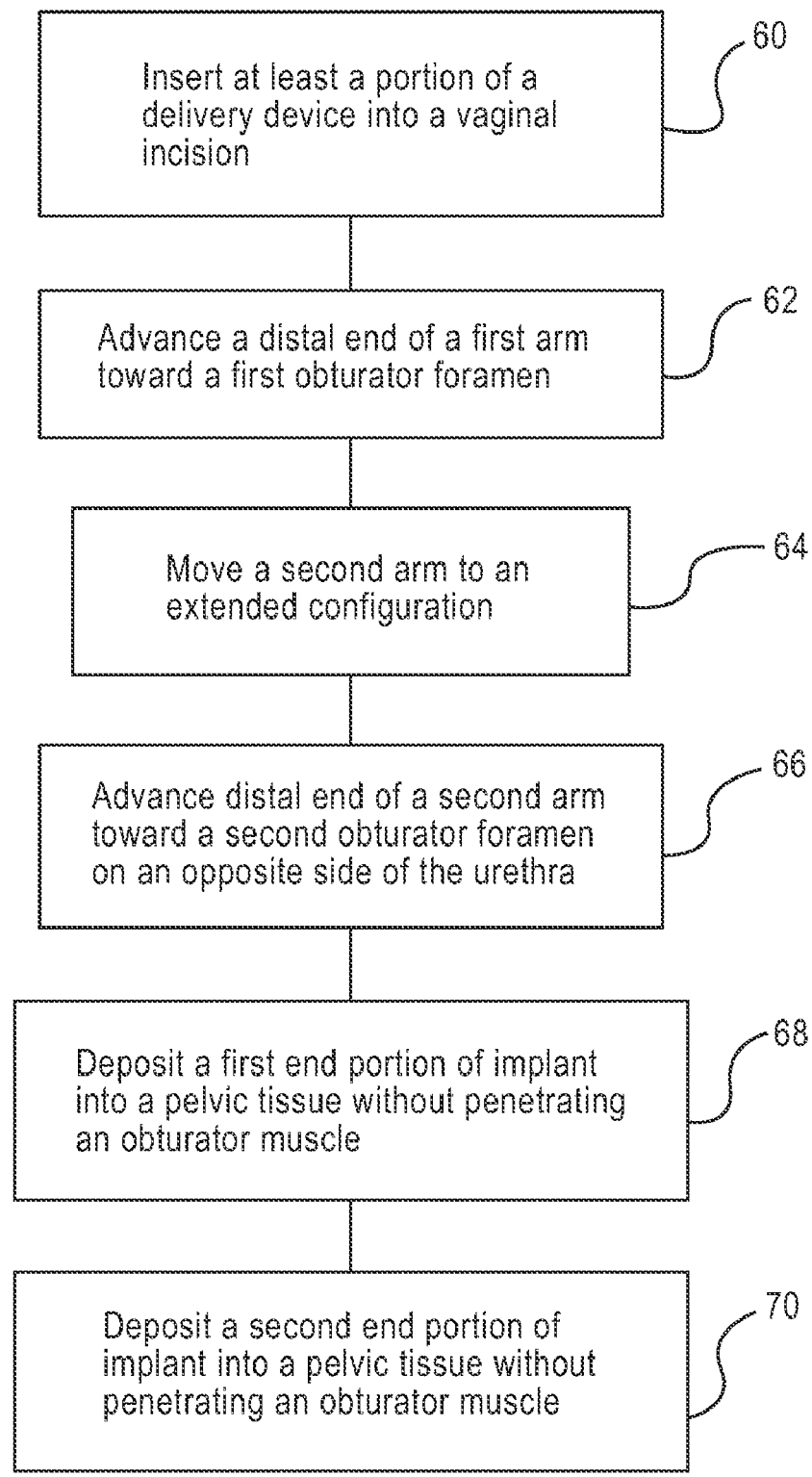
FIG. 21 is a flowchart of a method of placing an implant.

FIG. 21 is a flow chart illustrating a method of implanting a urethral implant. A method includes at 60, inserting at least a portion of a delivery device having an implant releasably coupled thereto into a vaginal incision in a patient. The implant can be delivered using any of the various approaches described herein (e.g., a retro pubic, pre-pubic approach or obturator approach). The delivery device has a first arm, and a second arm that is in a retracted position relative to the first arm during the inserting. At 62, a distal end of the first arm is advanced in a direction toward a first internal edge of an obturator foramen of the patient until a centerline of the medical implant is positioned substantially in line with a clitoris of the patient. At 64, the second arm is moved to an extended configuration. At 66, a distal end of the second arm is advanced toward a second internal edge of an obturator foramen on an opposite side of the urethra of the patient. For example, the second arm can be slid relative to the first arm along a path defined by a slot defined by the second arm.

At 68, a first end portion of the implant is deposited into a first portion of pelvic tissue without penetrating an obturator muscle; and at 70 a second end portion of the implant is deposited into a second portion of pelvic tissue without penetrating an obturator muscle such that a middle portion of the implant is positioned substantially below a urethra of the patient. In some embodiments, the first portion of tissue and second portion of tissue are each a portion of periurethral fascia. In some embodiments, the delivery device includes a handle, and the first arm and the second arm are each couplable to the handle. In some embodiments, prior to inserting the delivery device into the vaginal incision, the first end portion of the implant is releasably coupled to the first arm, and the second end portion of the implant is releasably coupled to the second arm.

In one embodiment, an apparatus that can be used to deliver an implant into a pelvic region includes a handle, a first arm coupled to the handle, and a second arm coupled to the handle and having a retracted configuration and an extended configuration. The first arm is configured to deposit a first end portion of an implant within a first portion of tissue in a pelvic region of a patient and the second arm is configured to deposit a second end portion of the implant to a second portion of tissue on an opposite side of a urethra when in an extended configuration, such that a portion of the implant is positioned substantially beneath the urethra.

The apparatus can further include a first coupling member coupled to the first arm that is configured to releasably couple the first end portion of the implant to the first arm. The apparatus according to one embodiment can further include a wire coupled to at least one of the first arm or the second arm and that is configured to couple at least one of the first end portion or the second end of the implant within a window defined by the at least one of the first arm or the second arm.

In some embodiments, the apparatus can further include a clamp coupled to at least one of the first arm or the second arm. The clamp is configured to couple at least one of the first end portion or the second end portion of the implant within a window defined by the at least one of the first arm or the second arm. In some embodiments, the apparatus can be configured such that the first arm has a sharpened distal end and the second arm has a sharpened distal end each configured to penetrate pelvic tissue. In some embodiments, the first arm, the second arm, or both the first and second arms are malleable.

In some embodiments, the first arm is configured to deposit a first end portion of an implant within a first portion periurethral tissue and the second arm is configured to deposit a second end portion of the implant within a portion of periurethral tissue disposed on an opposite side of the urethra. In some embodiments, the second arm is slidably coupled to the first arm. In some embodiments, the second arm defines a slot that is configured to slidably couple the second arm to the first arm. The slot defines a path of travel of the second arm relative to the first arm. In some embodiments the apparatus includes a handle coupled to the first arm, and in some embodiments, the first arm includes a handle portion.

In another embodiment, an apparatus includes a handle and a first arm couplable to the handle. A second arm is couplable to the handle and has a length that is less than a length of the first arm. The first arm is configured to releasably couple a first portion of an implant thereto. The second arm is configured to releasably couple a second portion of the implant thereto. The apparatus is configured to deliver the implant to a pelvic region of a patient and deposit the first end portion of the implant in a first tissue portion and the second end portion of the implant in a second tissue portion.

In some embodiments, the apparatus is configured to deposit the first end portion of the implant within a first portion of periurethral tissue, and the second end portion of the implant within a second portion of periurethral tissue. In some embodiments, the apparatus further includes a first coupling member coupled to the first arm that is configured to releasably couple the first end portion of the implant to the first arm.

In some embodiments, the apparatus further includes a wire coupled to at least one of the first arm or the second arm. The wire is configured to couple at least one of the first end portion or the second end portion of the implant within a window defined by the first arm or the second arm. In some embodiments, the apparatus further includes a clamp coupled to at least one of the first arm or the second arm. The clamp is configured to couple at least one of the first end portion or the second end portion of the implant within a window defined by the first arm or the second arm.

In some embodiments, the first arm and the second arm each have a sharpened distal end. In some embodiments, the first arm, the second arm or both the first arm and second arm are malleable.

In another embodiment, a method includes inserting at least a portion of a delivery device having an implant releasably coupled thereto into a vaginal incision in a patient. The delivery device has a first arm and a second arm. The second arm is in a retracted position during the inserting. A first end portion of the implant is deposited into a first portion of pelvic tissue. The second arm is moved to an extended configuration, and a second end portion of the implant is deposited into a second portion of pelvic tissue such that a middle portion of the implant is positioned substantially below a urethra of the patient.

In some embodiments, prior to the first end portion being deposited into pelvic tissue, a distal end of the first arm is advanced in a direction toward a first internal edge of an obturator foramen of the patient until a centerline of the implant is positioned substantially in line with a clitoris of the patient. In some embodiments, when the second end portion of the implant is deposited into tissue, the middle portion of the implant is positioned substantially below the urethra of the patient in a pre-pubic position.

In some embodiments, prior to the second end portion being deposited, a distal end of the second arm is advanced toward an internal edge of an obturator foramen of the patient. In some embodiments, when the second arm is moved to the extended configuration, the second arm is slid relative to the first arm along a path defined by a slot in the second arm. In some embodiments, prior to inserting the delivery device into the vaginal incision, the first end portion of the implant is releasably coupled to the first arm.

In another embodiment, a kit includes a delivery device that includes a first arm and a second arm. A mesh implant is included that is releasably couplable to the delivery device. The implant has a first end portion and a second end portion each configured to anchor the implant within pelvic tissue such that a middle portion of the implant is disposed beneath a urethra. The first arm defines a window through which a portion of the first end portion of the implant is disposable.

In some embodiments, the delivery device of the kit includes a first coupling member coupled to the first arm that is configured to releasably couple the first end portion of the implant within the window of the first arm. In some embodiments, the first arm has a length and the second arm has a length shorter than the length of the first arm. In some embodiments, the second arm is slidably coupled to the first arm. In some embodiments, the second arm defines a slot that is configured to slidably couple the second arm to the first arm. The slot defines a path of travel of the second arm relative to the first arm.

Conclusion

While various embodiments have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable a person skilled in the art to make and/or use the invention. While the invention has been particularly shown and described with reference to embodiments thereof, it will be understood by those skilled in art that various changes in form and details may be made therein without departing from the spirit and scope of the invention. For example, the various features of an implant (e.g., 20, 120, 220, etc.) may include other configurations, shapes and materials not specifically illustrated. An implant according to the invention can have a variety of different shapes and sizes, such as for example, circular, square, rectangular, elliptical, oval, diamond shaped, triangular, etc. An implant can also have various configurations of strengthening members, such as various different patterns, designs, lengths, sizes, etc.

In addition, a delivery device described herein (e.g., 24, 124, 224, etc.) can include various combinations and/or sub-combinations of the components and/or features of the different embodiments described. The delivery devices described herein can also be used to deliver and secure embodiments of pelvic implants not specifically described herein, such as implants having anchors and or sutures.

An implant according to any of the embodiments can be assembled to a delivery device by a user or provided preassembled. The implants can also be delivered using other delivery devices not described herein. In addition, although example approaches and tissue sites were described herein, it should be understood that the delivery devices can be used to deliver an implant using a variety of different approaches (e.g., pre-pubic, retro-pubic and/or obturator approaches), and the implant can be secured to a variety of different tissue sites within a pelvic region.

What is claimed is:

1. An apparatus, comprising:
a handle;
a first arm fixedly coupled to the handle;
a second arm coupled to the handle and having a retracted configuration and an extended configuration,
the first arm configured to deposit a first end portion of an implant within a first portion of pelvic tissue when the second arm is in the refracted configuration,
the second arm configured to deposit a second end portion of the implant to a second portion of pelvic tissue on an opposite side of a urethra when the second arm is in the extended configuration such that a portion of the implant is positioned substantially beneath the urethra; and
a coupling member coupled to the first arm, the coupling member being configured to couple the first end portion of the implant within a window defined by the first arm.

2. The apparatus of claim 1, wherein the coupling member is a wire.

3. The apparatus of claim 1, wherein the coupling member is a clamp.

4. The apparatus of claim 1, wherein the first arm has a sharpened distal end and the second arm has a sharpened distal end each configured to penetrate pelvic tissue.

5. The apparatus of claim 1, wherein at least one of the first arm or the second arm is malleable.

6. The apparatus of claim 1, wherein the first portion of pelvic tissue is a first portion of periurethral tissue, the second portion of pelvic tissue is a second portion of periurethral tissue disposed on an opposite side of the urethra.

7. The apparatus of claim 1, wherein the second arm is slidably coupled to the handle.

8. The apparatus of claim 1, wherein the second arm defines a slot configured to slidably couple the second arm to the handle, the slot defines a path of travel of the second arm relative to the handle.

9. An apparatus, comprising:
a handle;
a first arm having a length and being couplable to the handle, the first arm being configured to be releasably coupled to a first portion of an implant;
a second arm being couplable to the handle, the second arm having a length that is less than the length of the first arm, the second arm being configured to be releasably coupled to a second portion of the implant; and
a wire coupled to the first arm and configured to be threaded through the first portion of an implant to couple the first portion implant to the first arm,
the apparatus configured to deliver the implant to a pelvic region of a patient and deposit the first portion of the implant in a first tissue portion and the second portion of the implant in a second tissue portion.

10. The apparatus of claim 9, wherein the first portion of tissue is a first portion of periurethral tissue, the second portion of tissue is a second portion of periurethral tissue.

11. The apparatus of claim 9, wherein the first arm has a sharpened distal end and the second arm has a sharpened distal end.

12. The apparatus of claim 9, wherein at least one of the first arm or the second arm is malleable.

13. A method, comprising:
inserting a portion of an implant into a window defined by a first arm of a delivery device, the delivery device having the first arm fixedly coupled to a handle and a second arm movably coupled to the handle;
releasably coupling the first end portion of an implant to the first arm of the delivery device;
inserting at least a portion of the delivery device into a vaginal incision in a patient, the second arm being in a retracted position during the inserting;
depositing a first end portion of the implant into a first portion of pelvic tissue;
moving the second arm with respect to the handle to an extended configuration; and
depositing a second end portion of the implant into a second portion of pelvic tissue such that a middle portion of the implant is positioned substantially below a urethra of the patient.

14. The method of claim 13, further comprising:
prior to the depositing the first end portion, advancing a distal end of the first arm in a direction toward a first internal edge of an obturator foramen of the patient until a centerline of the implant is positioned substantially in line with a clitoris of the patient.

15. The method of claim 13, wherein the depositing the second end portion of the implant includes the middle portion of the implant being positioned substantially below the urethra of the patient in a pre-pubic position.

16. The method of claim 13, further comprising:
prior to depositing the second end portion, advancing a distal end of the second arm toward an internal edge of an obturator foramen of the patient.

17. The method of claim 13, wherein the moving the second arm to the extended configuration includes sliding the second arm relative to the handle along a path defined by a slot defined by the second arm.

18. A kit, comprising:
a delivery device including a first arm and a second arm; and
a mesh implant releasably couplable to the delivery device and having a first end portion and a second end portion each configured to anchor the implant within pelvic tissue such that a middle portion of the implant is disposed beneath a urethra,
the first arm defining a window through which a portion of the first end portion of the implant is disposable, the delivery device includes a first coupling member coupled to the first arm and configured to be threaded through the portion of the first end portion of the implant to releasably couple the implant to the first arm.

19. The kit of claim 18, wherein the first arm has a length and the second arm has a length shorter than the length of the first arm.

20. The kit of claim 18, wherein the second arm is slidably coupled to the first arm.

21. The kit of claim 18, wherein the second arm defines a slot configured to slidably couple the second arm to the first arm, the slot defines a path of travel of the second arm relative to the first arm.

* * * * *